United States Patent
Govari et al.

(10) Patent No.: US 11,185,366 B2
(45) Date of Patent: Nov. 30, 2021

(54) ESTIMATION OF TISSUE THICKNESS FROM RATE OF CHANGE OF CATHETER TEMPERATURE

(71) Applicant: BIOSENSE WEBSTER (ISRAEL) LTD., Yokneam (IL)

(72) Inventors: Assaf Govari, Haifa (IL); Israel Zilberman, Yokneam (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 374 days.

(21) Appl. No.: 15/896,687

(22) Filed: Feb. 14, 2018

(65) Prior Publication Data
US 2018/0263690 A1  Sep. 20, 2018

Related U.S. Application Data

(60) Provisional application No. 62/470,983, filed on Mar. 14, 2017.

(51) Int. Cl.
*A61B 18/14* (2006.01)
*A61B 5/107* (2006.01)
(Continued)

(52) U.S. Cl.
CPC .......... *A61B 18/1492* (2013.01); *A61B 5/01* (2013.01); *A61B 5/1076* (2013.01);
(Continued)

(58) Field of Classification Search
CPC ....... A61B 5/01; A61B 5/1072; A61B 5/1076; A61B 5/6885; A61B 18/1492;
(Continued)

(56) References Cited

U.S. PATENT DOCUMENTS 8,388,542 B2   3/2013 Zhang
8,388,549 B2 *  3/2013 Paul .................... A61B 5/6852
                                                  600/549
(Continued)

FOREIGN PATENT DOCUMENTS

EP      2 732 760 A1    5/2014
WO   WO 2016/168435 A1  10/2016

OTHER PUBLICATIONS

Farlow, Stanley J.. (1994). Introduction to Differential Equations and Their Applications—2.5.2 Constant Medium Temperature, (pp. 69). Dover Publications. Retrieved from https://app.knovel.com/hotlink/pdf/id:kt00B70HS4/introduction-differential/constant-medium-temperature (Year: 2013).*

(Continued)

*Primary Examiner* — Linda C Dvorak
*Assistant Examiner* — Nils A Potter
(74) *Attorney, Agent, or Firm* — Dergosits & Noah LLP; Todd A. Noah (57) ABSTRACT

Apparatus, consisting of a probe having a distal end that is configured to be inserted into contact with tissue. An electrode is attached to the distal end, and there is a temperature sensor incorporated in the distal end and configured to output a temperature signal. A radiofrequency (RF) signal generator is configured to apply a pulse of RF electrical energy via the electrode to the tissue, so as to heat the tissue. The apparatus includes processing circuitry that is configured to compute, based on the temperature signal, a rate of temperature change of the distal end following termination of the pulse, and to estimate a thickness of the tissue in response to the rate of temperature change.

6 Claims, 4 Drawing Sheets

(51) Int. Cl.
  *A61B 5/00* (2006.01)
  *A61B 5/01* (2006.01)
  *A61B 5/283* (2021.01)
  *A61B 1/00* (2006.01)
  *A61B 18/00* (2006.01)

(52) U.S. Cl.
  CPC .......... *A61B 5/6852* (2013.01); *A61B 5/6885* (2013.01); *A61B 5/283* (2021.01); *A61B 2018/00351* (2013.01); *A61B 2018/00577* (2013.01); *A61B 2018/00642* (2013.01); *A61B 2018/00702* (2013.01); *A61B 2018/00761* (2013.01); *A61B 2018/00791* (2013.01); *A61B 2018/00839* (2013.01); *A61B 2218/002* (2013.01); *A61B 2505/05* (2013.01)

(58) Field of Classification Search
  CPC ........... A61B 2018/00577; A61B 2018/00791; A61B 2218/002
  USPC .......................................................... 606/34
  See application file for complete search history.

(56) References Cited

U.S. PATENT DOCUMENTS

| | | |
|---|---|---|
| 2004/0267191 A1 | 12/2004 | Gifford |
| 2012/0232339 A1 | 9/2012 | Csiky |
| 2012/0302882 A1* | 11/2012 | Sliwa ...................... A61B 8/12 600/439 |
| 2014/0171936 A1 | 6/2014 | Govari et al. |
| 2015/0088116 A1* | 3/2015 | Wham ............... A61B 18/1445 606/34 |
| 2016/0249174 A1* | 8/2016 | Patel ................... H04W 64/006 |
| 2017/0014181 A1 | 1/2017 | Bar-Tal et al. |

OTHER PUBLICATIONS

European Search Report dated Jul. 2, 2018 from corresponding European Patent Application No. 18161510.5.
Hussein, Ahmed et al., "Ablation Index-guided Pulmonary Vein Isolation for Atrial Fibrillation may Improve Clinical Outcomes in Comparison to Contact Force-guided Ablation", Heart Rhythm Congress, Oct. 12, 2016, page ii14.

* cited by examiner

TISSUE THICKNESS D (mm)

A 0.63A

B s, $\left[\frac{\Delta T}{\Delta t}\right]$ NORM (°C/s)

NORMALIZED RATE OF TEMPERATURE CHANGE AT DISTAL END

FIG. 4

ESTIMATION OF TISSUE THICKNESS FROM RATE OF CHANGE OF CATHETER TEMPERATURE

CROSS-REFERENCE TO RELATED APPLICATION

This application claims the benefit of U.S. Provisional Patent Application 62/470,983, filed Mar. 14, 2017, which is incorporated herein by reference.

FIELD OF THE INVENTION

This invention relates generally to measurements of biological tissue, and specifically to measuring the thickness of the tissue.

BACKGROUND OF THE INVENTION

During medical procedures performed on tissue, such as acquisition of a biopsy or ablation of a portion of the myocardium, it may be useful to know the thickness of the tissue. In a number of cases this may be deduced from a pre-acquired image of the tissue, such as from an MRI (magnetic resonance imaging) or a CT (computerized tomography) image. In the case of ablation, this data may not be available to the professional performing the ablation. Even if it is available, it may not give the thickness to sufficient accuracy, or the thickness may have changed since acquisition of the image.

SUMMARY OF THE INVENTION

An embodiment of the present invention provides an apparatus, including:

a probe having a distal end configured to be inserted into contact with tissue;

an electrode attached to the distal end;

a temperature sensor incorporated in the distal end and configured to output a temperature signal;

a radiofrequency (RF) signal generator configured to apply a pulse of RF electrical energy via the electrode to the tissue, so as to heat the tissue; and processing circuitry configured to compute, based on the temperature signal, a rate of temperature change of the distal end following termination of the pulse, and to estimate a thickness of the tissue in response to the rate of temperature change.

Typically, estimating the thickness of the tissue assumes the rate of temperature change increases as the thickness increases.

In a disclosed embodiment, estimating the thickness includes assuming a mathematical relationship between the tissue thickness and the rate of temperature change, and the mathematical relationship includes parameters depending on thermal characteristics of the distal end.

In a further disclosed embodiment the rate of temperature change is a function of a force applied by the distal end to the tissue, a power level applied by the generator, a length of time of the pulse, and an irrigation rate of fluid irrigating the tissue. Typically the rate of temperature change includes a normalized rate of temperature change determined assuming a direct proportionality for the force, the power level, and the length of time of the pulse, and an inverse proportionality for the irrigation rate.

In a yet further disclosed embodiment applying the pulse includes applying a preset RF power level for a first preset time period, and computing the rate of temperature change includes recording the temperature signal for a second preset time period beginning on termination of the pulse.

In an alternative embodiment the circuitry is configured to set a power level to be supplied by the RF signal generator for ablation of the tissue, and a time for the ablation, in response to the estimated thickness of the tissue.

There is further provided, according to an embodiment of the present invention, a method, including:

inserting a distal end of a probe into contact with tissue;

attaching an electrode to the distal end;

incorporating a temperature sensor, configured to output a temperature signal, in the distal end;

configuring a radiofrequency (RF) signal generator to apply a pulse of RF electrical energy via the electrode to the tissue, so as to heat the tissue; and computing, based on the temperature signal, a rate of temperature change of the distal end following termination of the pulse, and estimating a thickness of the tissue in response to the rate of temperature change.

The present disclosure will be more fully understood from the following detailed description of the embodiments thereof, taken together with the drawings, in which:

DETAILED DESCRIPTION OF EMBODIMENTS

Overview

Embodiments of the present invention provide an independent measure of the thickness of tissue being investigated, typically in an investigation comprising an ablation procedure. For an ablation procedure the method may be applied while ablation is actually being performed, or while no ablation is occurring. The measure relies on the discovery by the inventor that if a heat energy pulse is injected into tissue from the distal end of a catheter in contact with the tissue, the rate of change of the temperature of the distal end varies according to the thickness of the tissue. I.e., for thick tissue the rate is large, and for thin tissue the rate is small.

Thus, in a typical procedure using radiofrequency energy for ablating tissue, a catheter distal end is inserted into contact with the tissue to be ablated, and the distal end and the tissue are irrigated at a given rate. During the irrigation a radiofrequency pulse is applied for a short time to the tissue, and the temperature of the catheter distal end, typically a mean temperature calculated from multiple sensors in the distal end, is monitored. The thickness of the tissue is then estimated from the measured rate of change of the temperature of the distal end. The estimation typically comprises using a relationship between a normalized rate of change of the temperature of the distal end and the thickness of the tissue. The relationship may be determined prior to insertion of the catheter into proximity with the tissue.

Once the tissue thickness has been estimated, the value of the thickness may be used in estimating the power to be used for the ablation, and the time period over which the power is to be applied, in order to achieve a successful ablation of the tissue.

DETAILED DESCRIPTION

Figure 1:
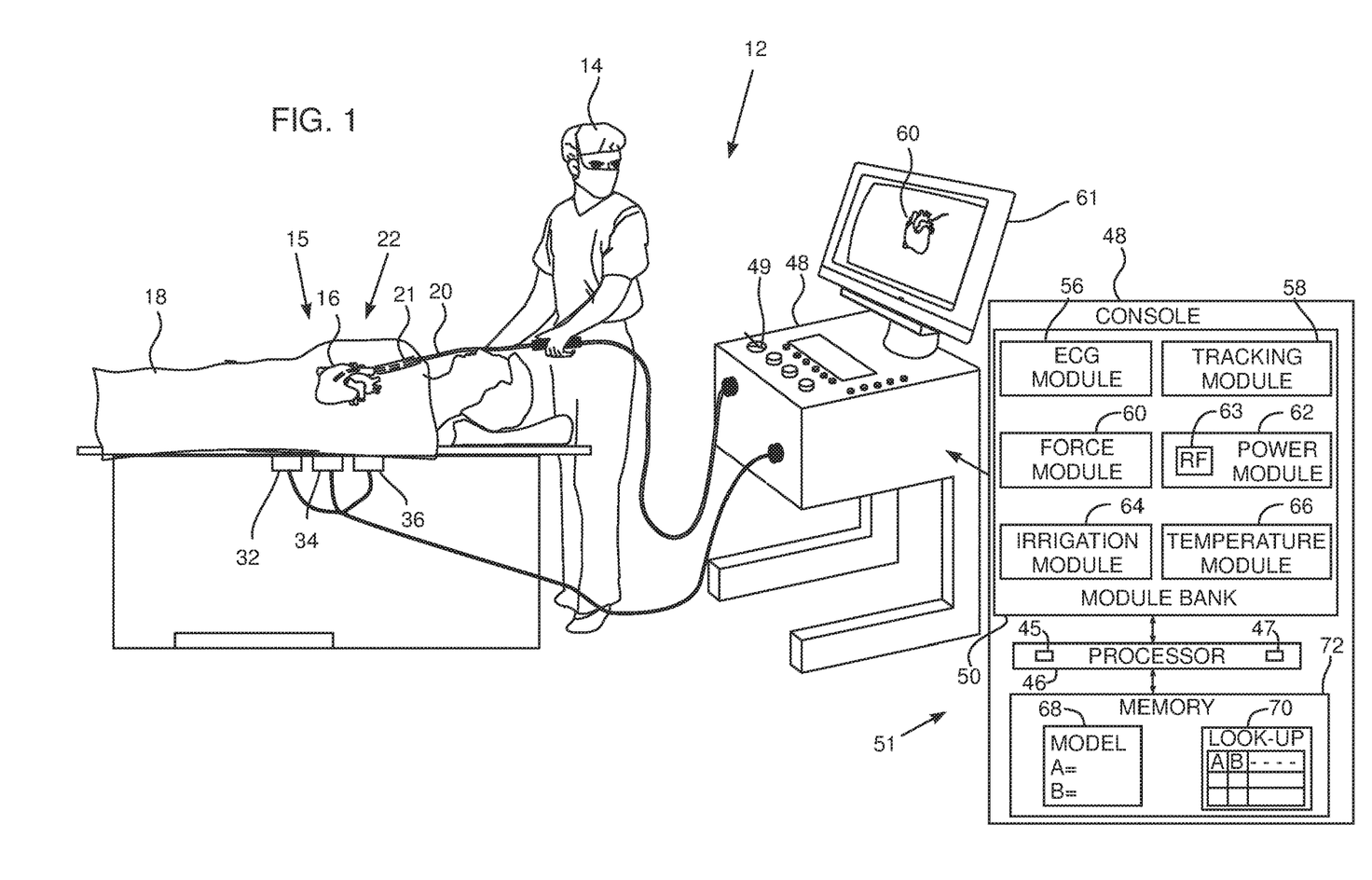
FIG. 1 is a schematic illustration of an invasive medical procedure using apparatus, according to an embodiment of the present invention.
Figure 2:
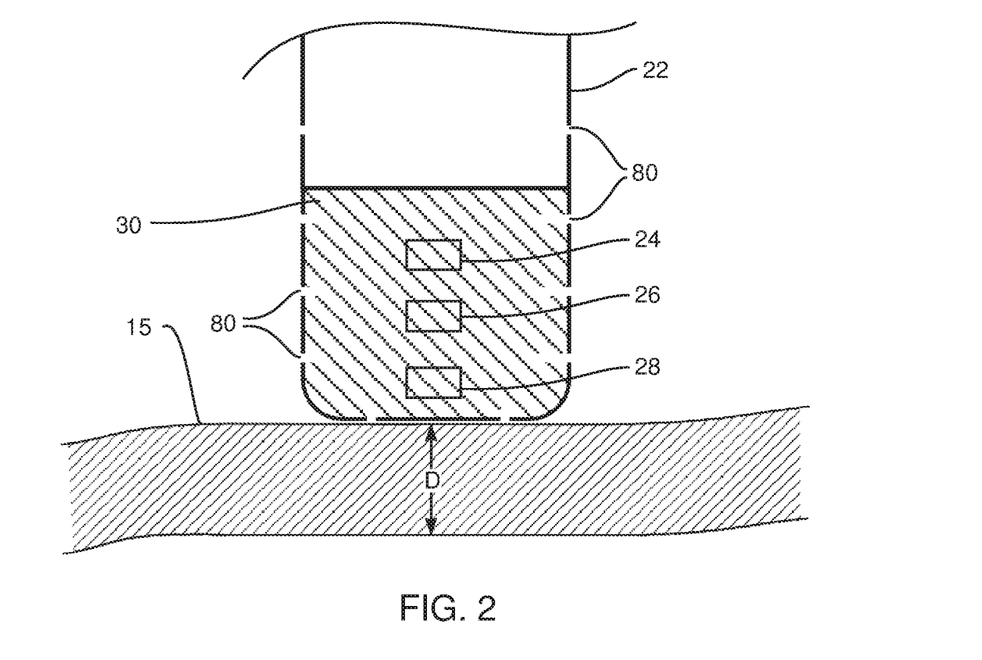
FIG. 2 is a schematic illustration of a distal end of a probe used in the apparatus, according to an embodiment of the present invention.

FIG. 1 is a schematic illustration of an invasive medical procedure using apparatus 12, and FIG. 2 is a schematic illustration of a distal end 22 of a probe 20 used in the apparatus, according to an embodiment of the present invention. The procedure is performed by a medical professional 14, and in the description hereinbelow the procedure is assumed to comprise an ablation of a portion of tissue 15 of a myocardium 16 of the heart of a human patient 18.

In order to perform the investigation, professional 14 inserts probe 20 into a sheath 21 that has been pre-positioned in a lumen of the patient. Sheath 21 is positioned so that distal end 22 of the probe enters the heart of the patient. Distal end 22 comprises a position sensor 24 that enables the location and orientation of the distal end to be tracked, a force sensor 26 that measures the force applied by the distal end when it contacts the myocardium, and one or more temperature sensors 28 that measure the temperature at respective locations of the distal end. Distal end 22 also comprises an electrode 30 which is used to deliver radiofrequency ablation power to myocardium 16 in order to ablate the myocardium. Electrode 30 may also be used to acquire electropotentials from the myocardium, as noted below.

Apparatus 12 is controlled by a system processor 46, which is located in an operating console 48 of the apparatus. Console 48 comprises controls 49 which are used by professional 14 to communicate with the processor. The software for processor 46 may be downloaded to the processor in electronic form, over a network, for example. Alternatively or additionally, the software may be provided on non-transitory tangible media, such as optical, magnetic, or electronic storage media. The track of distal end 22 is typically displayed on a three-dimensional representation 60 of the heart of patient 18 that is displayed on a screen 61.

System processor 46 comprises real-time noise reduction circuitry 45, typically configured as a field programmable gate array (FPGA), followed by an analog-to-digital (A/D) signal conversion integrated circuit 47. The processor can pass the signal from A/D circuit 47 to another processor and/or can be programmed to perform at least one algorithm disclosed herein, the algorithm comprising steps described hereinbelow. The processor uses circuitry 45 and circuit 47, as well as features of modules which are described in more detail below, in order to perform the algorithm.

In order to operate apparatus 12, the algorithm of processor 46 communicates with a module bank 50, which has a number of modules used by the processor to operate the apparatus. Thus, bank 50 comprises an electrocardiograph (ECG) module 56 which acquires and analyzes signals from electrode 30, and a tracking module 58 which receives and analyzes signals from position sensor 24, and which uses the signal analysis to generate a location and an orientation of distal end 22. In some embodiments sensor 24 comprises one or more coils which provide the sensor signals in response to magnetic fields traversing the coils. In these embodiments, in addition to receiving and analyzing signals from sensor 24, tracking module 58 also controls radiators 32, 34, and 36 which radiate the magnetic fields traversing sensor 24. The radiators are positioned in proximity to myocardium 16, and are configured to radiate alternating magnetic fields into a region in proximity to the myocardium. The Carto® system produced by Biosense Webster, of 33 Technology Drive, Irvine, Calif. 92613 USA, uses such a magnetic tracking system.

Bank 50 also comprises a force module 60, a power module 62, an irrigation module 64, and a temperature module 66. The functions of these modules are explained below. The modules in bank 50, and processor 46, are herein termed processing circuitry 51.

Force module 60 receives signals from force sensor 26, and from the signals generates a magnitude CF of the contact force, herein assumed to be measured in grams-force, exerted by distal end 22 on tissue 15. In some embodiments the force sensor 26 is configured so that the signals it provides to module 60 enable the module to evaluate a direction of the force exerted by the distal end on tissue 15.

Power module 62 comprises a radiofrequency (RF) signal generator 63 which generates the radiofrequency power that is conveyed to electrode 30, and that is applied by the electrode to ablate tissue 15. Processor 46 and module 62 are able to adjust a power level P, herein assumed to be measured in Watts, delivered by the electrode, as well as a length of time t, measured in seconds, during which the power is delivered, as described in more detail below.

Irrigation module 64 controls a rate of flow V, herein assumed to be measured in mL/min, of irrigation fluid, typically normal saline solution, supplied to distal end 22. The irrigation fluid is expelled from irrigation holes 80 in the distal end.

Temperature module 66 receives signals from one or more temperature sensors 28, and determines the temperatures registered by each of the sensors. Typically, in the case of multiple sensors 28 the module determines a mean temperature T of distal end 22. Additionally, in the case of multiple sensors, the module may produce a map of the temperature distribution of the distal end.

The inventor has found that on injection of a heat energy pulse into tissue 15 an overall thickness D of the tissue affects the rate of change of temperature $$\frac{\Delta T}{\Delta t}$$

measured by one or more sensors 28. In particular, for a given irrigation rate V of fluid through the distal end, and for a given contact force CF applied to the tissue by the distal end, the rate of change of temperature $$\frac{\Delta T}{\Delta t}$$

is large for large values of D and is small for small values of D, i.e., the rate of change of temperature increases as the thickness D increases. The heat energy pulse may be injected into the tissue by applying a radiofrequency energy pulse for a short time to the tissue. The inventor believes that the relationship described above, between the rate of change of temperature $$\frac{\Delta T}{\Delta t}$$

and the overall tissue thickness D, is due to the heat energy retained by the tissue. I.e., tissue having a large D retains more heat energy than tissue having a small D.

The relationship may be expressed by the following equation (1):

$$D = f\left(\frac{\Delta T}{\Delta t}\right) \quad (1)$$

where D is the thickness of the tissue,

ΔT is the change of temperature of the distal end in a time period Δt, and f is a function.

In one embodiment, the function f is as given in equation (2):

$$D = A\left(1 - e^{-\frac{s}{B}}\right)^n \quad (2)$$

where n is a numerical exponent,

A, B are constant parameters having values which depend on the thermal characteristics of the distal end of the catheter, and s is a normalized slope of a temperature-time graph, i.e., $$s = \left[\frac{\Delta T}{\Delta t}\right]_{NORM} \quad (2a)$$

The non-normalized slope of the temperature-time graph, $$\frac{\Delta T}{\Delta t},$$

depends on the contact force CF applied by the distal end to the tissue, the level P of the radiofrequency pulse power applied, the length of time t of application of the radiofrequency power pulse, and the irrigation rate V.

The non-normalized slope, $$\frac{\Delta T}{\Delta t},$$

is converted to a normalized slope, $$\left[\frac{\Delta T}{\Delta t}\right]_{NORM},$$

by normalizing CF to a normalized contact force $CF_{NORM}$, P to a normalized pulse power $P_{NORM}$, t to a normalized a pulse length $t_{NORM}$, and V to a normalized irrigation rate $V_{NORM}$. The normalization assumes respective relationships between the non-normalized slope and the contact force CF, the P pulse power P applied, the pulse length t, and the irrigation rate V. In an embodiment the relationships for CF, P, and t are assumed to comprise respective direct proportionalities, and the relationship for V is assumed to comprise an inverse proportionality. However, other relationships, that may be used in normalizing the slope of the temperature-time graph, will be apparent to those having ordinary skill in the art, and all such relationships are assumed to be comprised within the scope of the present invention.

In an embodiment the numerical exponent n in equation (2) is set as 1 or 2. In other embodiments the value for n may be set to be different from 1 and 2, and may be a non-integer value.

Values of A and B, as well as the normalized values referred to above, and values of the parameters of the relationships for normalizing the slope $$\frac{\Delta T}{\Delta t},$$

may be stored as a model 68 and/or in a look-up table 70 contained in a memory 72 that is accessed by processor 46.

Figure 3:
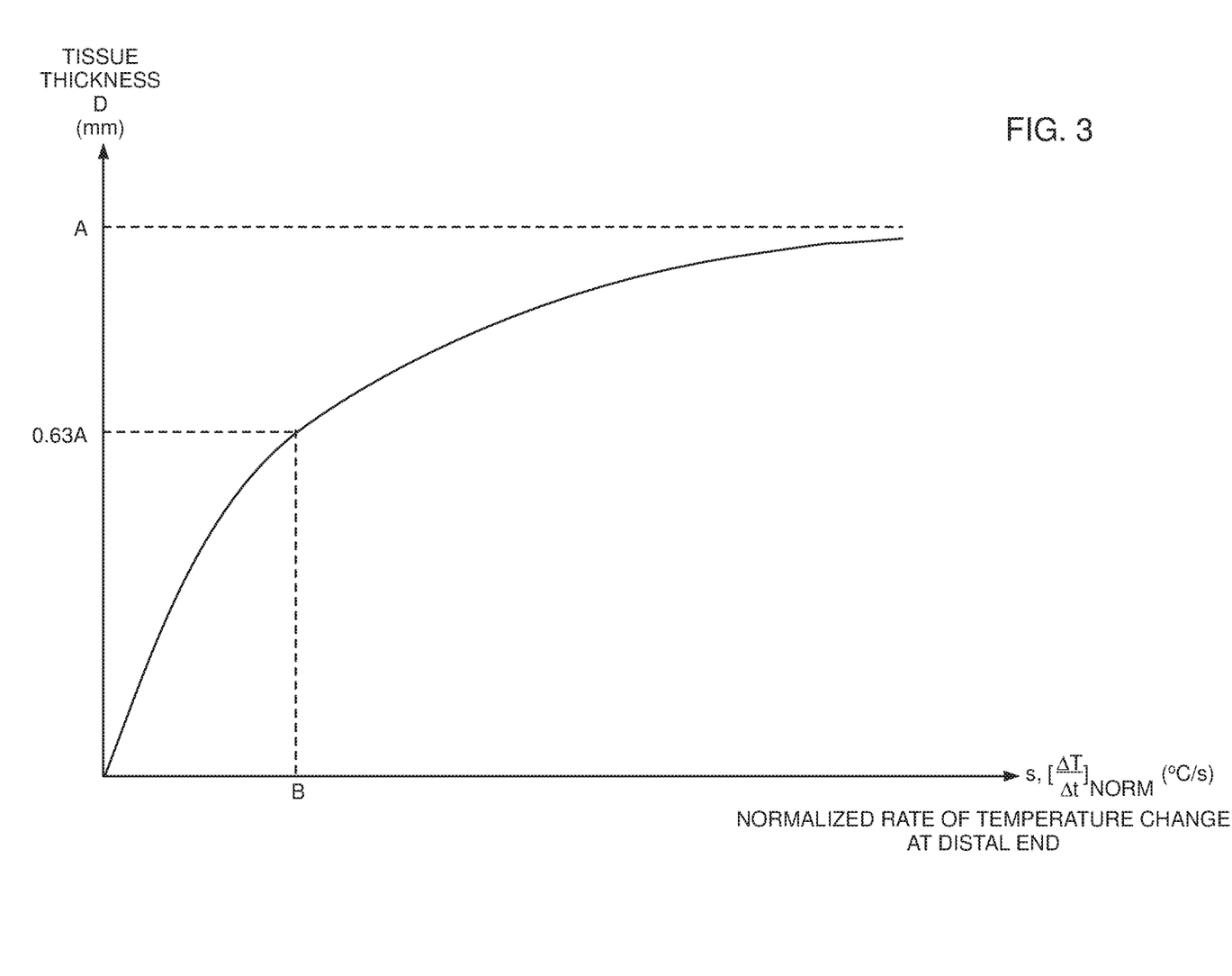
FIG. 3 is a schematic graph of tissue thickness vs. slope, according to an embodiment of the present invention.

FIG. 3 is a schematic graph of D vs. s, as determined from equation (2), for n=1, according to an embodiment of the present invention. As is illustrated in the graph, the slope s, $$\left[\frac{\Delta T}{\Delta t}\right]_{NORM},$$

i.e., the normalized rate of temperature change, increases monotonically with respect to the tissue thickness D. As is also illustrated, the graph exponentially approaches an asymptote D=A as the slope s increases, and for a normalized rate of temperature change of B, the thickness D is equal to 0.63 Å.

For clarity and simplicity, except where otherwise stated, the following description assumes that the relationship between the tissue thickness and the rate of change of temperature is as given by equation (2) with n=1. Those having ordinary skill in the art will be able to modify the description, mutatis mutandis, for other values of n and for other relationships of the form of equation (1).

Prior to performing an actual ablation procedure, professional 14 may determine values for A and B in equation (2), as well as values for the relationships used for normalizing the slope $$\frac{\Delta T}{\Delta t},$$

by ablation of tissue using measured values of tissue thickness D and slope $$\frac{\Delta T}{\Delta t}.$$

Typically such a determination involves using a range of values of irrigation rate V, radiofrequency pulse power P, length of time t of the pulse, and contact force CF. The values of P, V, and t are typically chosen so that the temperature of the tissue being used remains within a range of approximately 40° C.-60° C., so that any change of temperature is not harmful to the tissue.

In one embodiment the values for V are set within a range 10-20 mL/min, the values of P are set within a range of 20-30 W, the pulse length t is set within a range of 1-3 s, the contact force CF is within a range of 5-25 grams-force, and the normalized values are set at $V_{NORM}$=15 mL/min, $P_{NORM}$=25 W, $t_{NORM}$=2 s, and $CF_{NORM}$=15 grams-force. However, providing that the temperature of the tissue being used remains between approximately 40° C.-60° C., V, P, and t may have values outside these ranges, and the normalized values may be different from those provided here, and such alternative values may be determined by one with ordinary skill in the art without undue experimentation.

To determine A and B for a selected catheter, the distal end of the catheter is brought into contact with tissue of a known thickness D, and the distal end is configured to exert the normalized contact force $CF_{NORM}$ on the tissue while the distal end and tissue are irrigated at the normalized irrigation rate $V_{NORM}$. A radiofrequency pulse with the normalized power $P_{NORM}$ and pulse length $t_{NORM}$ is applied to the tissue, and the temperature T of the distal end is recorded as it changes over time. From the recordation of the distal end temperatures and times, an estimate of the normalized slope, $$\left[\frac{\Delta T}{\Delta t}\right]_{NORM},$$

is made. In one embodiment the value of $$\left[\frac{\Delta T}{\Delta t}\right]_{NORM}$$

is calculated from the change of temperature ΔT for a value of Δt of 5 s, where the value Δt is taken over the first 5 s of recordation.

The above determination is repeated for different values of tissue thickness D, giving respective different values of $$\left[\frac{\Delta T}{\Delta t}\right]_{NORM},$$

to get A and B values for the selected catheter.

For each selected catheter. professional 14 may use processor 46 to store the respective values of A, B, as mathematical model 68 (FIG. 1). Model 68 is a mathematical function, such as a cost function, that enables the processor to determine values of A and B from the experimental values of V, P, t and CF, together with values for the respective normalizing relationships to the normalized values $V_{NORM}$, $P_{NORM}$, $t_{NORM}$ and $CF_{NORM}$, as described above. Alternatively or additionally, professional 14 may configure the processor to store the respective values of A and B for each selected catheter, as well as the values for the respective relationships in a look-up table 70.

Figure 4:
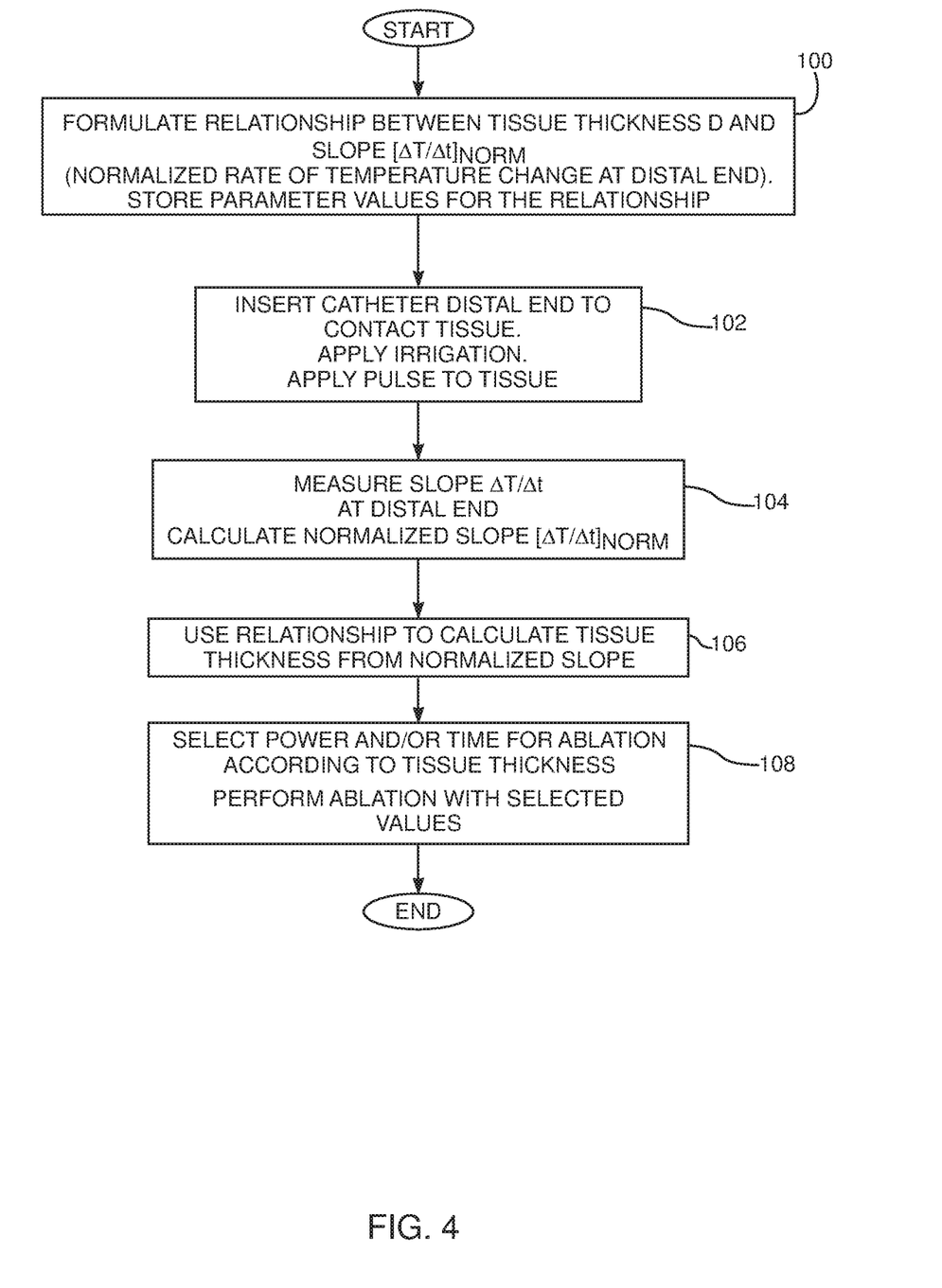
FIG. 4 is a flowchart of steps followed by a professional in performing the procedure, according to an embodiment of the present invention.

FIG. 4 is a flowchart of steps followed by professional 14 and the algorithm of processor 46 in performing the ablation procedure referred to above, according to an embodiment of the present invention. In a preparatory step 100 that is typically performed before the start of the ablation procedure, the relationship between tissue thickness D and normalized slope s, i.e., the normalized rate of temperature change $$\left[\frac{\Delta T}{\Delta t}\right]_{NORM}$$

of distal end 22, is formulated. As stated above, for simplicity and clarity the relationship herein is assumed to correspond to equation (2) with n=1. In addition to formulating the relationship, in step 100 values for parameters of the relationship, in this case A and B, as well as parameters for the normalizing relationships are stored as look-up table 70 and/or mathematical model 68, as described above. Typically a catheter having a distal end similar to the distal end 22 that is used in the ablation procedure of the present flowchart is used to perform the evaluations and/or generate look-up table 70 and mathematical model 68.

In an initial procedure step 102, professional 14 inserts distal end 22 to contact a selected portion of tissue 15 of myocardium 16, and force module 60 and processor 46 record a contact force CF sensed by force sensor 26. Once in contact with tissue 15, the professional sets a flow rate V of irrigation to the distal end. Typically, the value for V is set within a range 10-20 mL/min, but V may have a value outside this range. In addition, while the distal end and the tissue are being irrigated, the processor uses electrode 30 to apply a radiofrequency power pulse to the tissue in contact with the distal end. In one embodiment the processor sets the pulse to have a power P of 30 Watts and a duration t of 1 second. The processor records the values of V, P, and t.

In a slope measurement step 104, once the pulse has been applied to tissue 15, the processor begins recording the temperature of the one or more temperature sensors 28, as well as the times of recordation. From the temperatures and the times, the processor evaluates a value of the slope $$\frac{\Delta T}{\Delta t}.$$

From the slope, the processor calculates the normalized rate of temperature change $$\left[\frac{\Delta T}{\Delta t}\right]_{NORM},$$

i.e., the normalized slope of the corresponding temperature-time graph, of distal end 22.

In a tissue thickness step 106, the processor applies the normalized slope found in step 104 to the relationship formulated in step 100, together with appropriate values for parameters A, B, of the relationship, to evaluate a thickness D of tissue 15. For the relationship corresponding to equation (2) with n=1, the values of A and B are found from look-up table 70 and/or mathematical model 68.

In an ablation step 108 the processor uses the evaluated tissue thickness D to estimate a radiofrequency power P and a duration time t for which the power is to be applied, to ablate tissue 15. The estimation typically uses an ablation index, described below.

As is known in the art, an ablation index is a function, having a value that changes as ablation proceeds, which provides an estimate of the size of a lesion produced by the ablation of a tissue of known type. The estimate provided by the index depends on the values of the contact force CF and power P measured during the ablation, as well as on the period of time of the ablation. Ablation indices are described in an article entitled "Ablation Index-guided Pulmonary Vein Isolation for Atrial Fibrillation may Improve Clinical Outcomes in Comparison to Contact Force-guided Ablation" to Hussein et al., presented at the 2016 Heart Rhythm Congress, and in U.S. Patent Application 2017/0014181 to Bar-Tal et al. Both documents are incorporated herein by reference.

Equation (3) below gives an expression for an ablation index:

$$D=(C\int_0^t CF^\alpha(\tau)P^\beta(\tau)d\tau)^\delta \equiv \text{Ablation Index} \quad (3)$$

where C is a constant having a value depending on the type of tissue being ablated; in one embodiment C has an approximate value of 0.002, $\alpha$ is an exponent having a value typically in the range 0.6-0.8, $\beta$ is an exponent having a value typically in the range 1.4-1.8, $\delta$ is an exponent having an approximate value of 0.35, and D is an estimate of the depth of a lesion achieved by ablating for a time t, with instantaneous contact force $CF(\tau)$ and instantaneous power $P(\tau)$, and where $\tau$ represents a time variable.

If the contact force and the power are assumed to be constant, having respective values $\overline{CF}$ and $\overline{P}$ during an ablation procedure that is to take a time t, then equation (3) may be rewritten as equation (4):

$$D=(C\overline{CF}^\alpha \overline{P}^\beta t)^\delta \quad (4)$$

The value of the left side of equation (4), tissue thickness D, is known from step 106. Processor 46 may thus use the right side of equation (4) to provide to professional 14 recommended values of power P and time t for ablation using the measured value of force CF and an estimate of C.

In step 108 professional 14 selects one of the recommended values of power P and time t to ablate tissue 15, and concludes the ablation of tissue 15 with these values.

The description above of steps of the flowchart assumes that professional 14 uses an ablation index in determining values of power to be applied during an ablation procedure. The ablation index acts as an aid to the professional in deciding values of parameters, such as power and time period of ablation, to be used during an ablation procedure. However, it will be understood that the professional may not use an ablation index in deciding values of such parameters, while still using the description of tissue thickness step 106 to estimate the thickness of tissue being ablated, and may adapt the flowchart description, mutatis mutandis, for such a case. It will thus be understood that the scope of the present invention includes cases where an ablation index is not used.

The description above has also assumed that the rate of change of temperature of the catheter distal end, i.e., the slope of the temperature-time graph, is normalized. Nevertheless, those having ordinary skill in the art will be able to adapt the description to accommodate cases where the rate of change of temperature of the catheter distal end is not normalized.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus for measuring tissue thickness, the apparatus comprising:
   a probe having a distal end configured to be inserted into contact with tissue;
   an electrode attached to the distal end;
   a temperature sensor incorporated in the distal end and configured to output a temperature signal;
   an irrigation module configured to apply an irrigation fluid at a predetermined rate of flow;
   a radiofrequency (RF) signal generator configured to apply a pulse of RF electrical energy via the electrode to the tissue, the RF electrical energy applied at a preset RF power level and for a first preset time period so as to heat the tissue during application of the irrigation fluid flowing at the predetermined rate; and
   processing circuitry configured to compute, based on the temperature signal, the temperature signal being recorded for a second preset time period beginning at the termination of the pulse of RF energy, a rate of temperature change of the distal end of the probe following termination of the pulse, and to estimate a thickness of the tissue in response to the rate of temperature change of the probe, wherein the rate of temperature change is a function of and comprises a normalized rate of temperature change determined by assuming a direct proportionality of a force applied by the distal end to the tissue, a power level applied by the generator, a length of time of the pulse, and an inverse proportionality for the irrigation rate of fluid irrigating the tissue and wherein the estimation of tissue thickness is also a function of the thermal characteristics of the distal end of the probe.

2. The apparatus according to claim 1, wherein estimating the thickness of the tissue comprises assuming the rate of temperature change increases as the thickness increases.

3. The apparatus according to claim 1, wherein the circuitry is configured to set a power level to be supplied by the RF signal generator for ablation of the tissue, and a time for the ablation, in response to the estimated thickness of the tissue.

4. A method for measuring tissue thickness, the method comprising:
   inserting a distal end of a probe into contact with tissue;
   attaching an electrode to the distal end;
   incorporating a temperature sensor, configured to output a temperature signal, in the distal end;
   configuring an irrigation module to apply an irrigation fluid at a predetermined rate of flow;
   configuring a radiofrequency (RF) signal generator to apply a pulse of RF electrical energy via the electrode to the tissue, the RF electrical energy applied at a preset RF power level and for a first preset time period so as to heat the tissue during application of the irrigation fluid flowing at the predetermined rate; and
   computing, based on the temperature signal, the temperature signal being recorded for a second preset time period beginning at the termination of the pulse of RF energy, a rate of temperature change of the distal end of the probe following termination of the pulse, and estimating a thickness of the tissue in response to the rate of temperature change of the probe, wherein the rate of temperature change is a function of and comprises a normalized rate of temperature determined by assuming a direct proportionality of a force applied by the distal end to the tissue, a power level applied by the generator, a length of time of the pulse, and an inverse proportionality for an irrigation rate of fluid irrigating the tissue and wherein the estimation of tissue thickness is also a function of the thermal characteristics of the distal end of the probe.

5. The method according to claim 4, wherein estimating the thickness of the tissue comprises assuming the rate of temperature change increases as the thickness increases.

6. The method according to claim 4, wherein the circuitry is configured to set a power level to be supplied by the RF signal generator for ablation of the tissue, and a time for the ablation, in response to the estimated thickness of the tissue.

\* \* \* \* \*